United States Patent
Lemonis et al.

(10) Patent No.: US 10,238,539 B2
(45) Date of Patent: Mar. 26, 2019

(54) TECHNIQUE FOR CONTROLLING A CORNEAL ABLATION LASER

(75) Inventors: Sissimos Lemonis, Schwaig (DE); Alexander Kempe, Berlin (DE); Mario Abraham, Burgthann (DE); Peter Riedel, Nuremberg (DE)

(73) Assignee: Wavelight GmbH (DE)

(*) Notice: Subject to any disclaimer, the term of this patent is extended or adjusted under 35 U.S.C. 154(b) by 292 days.

(21) Appl. No.: 14/378,367

(22) PCT Filed: Apr. 20, 2012

(86) PCT No.: PCT/EP2012/001727
§ 371 (c)(1),
(2), (4) Date: Nov. 20, 2014

(87) PCT Pub. No.: WO2013/156046
PCT Pub. Date: Oct. 24, 2013

(65) Prior Publication Data
US 2015/0116725 A1 Apr. 30, 2015

(51) Int. Cl.
*A61F 9/008* (2006.01)
*G01B 9/02* (2006.01)
*A61B 3/10* (2006.01)

(52) U.S. Cl.
CPC .......... *A61F 9/00804* (2013.01); *A61B 3/102* (2013.01); *A61F 9/00802* (2013.01);
(Continued)

(58) Field of Classification Search
CPC ............ G01B 9/02091; G01B 9/02049; A61F 2009/00844; A61F 2/1637;
(Continued)

(56) References Cited

U.S. PATENT DOCUMENTS 6,245,059 B1 * 6/2001 Clapham ................. A61F 9/008
128/898
2003/0020874 A1 * 1/2003 J. Smith ................... A61B 3/11
351/204

(Continued)

FOREIGN PATENT DOCUMENTS

CA 2729249 C 8/2014
EP 1923027 A1 5/2008

(Continued)

OTHER PUBLICATIONS

Wikipedia; Corneal topography; from Apr. 10, 2012, downloaded on May 1, 2018; 3 pages; Retrieved from website: https://en.wikipedia.org/w/index.php?title=Corneal_topography&oldid=486685587.

(Continued)

*Primary Examiner* — Gary Jackson
*Assistant Examiner* — Jonathan Kuo
(74) *Attorney, Agent, or Firm* — Keiko Ichiye, Esq.

(57) ABSTRACT

A technique for controlling a corneal ablation laser is described. As to a device aspect of the technique, a device comprises a parameter interface, a first determination unit, a second determination unit, a computation unit, and a control unit. The parameter interface receives an adjustment parameter. The first determination unit determines a first point on a corneal surface. The second determination unit determines a second point on the corneal surface that is different from the first point. The computation unit determines a third point on a line between the first point and the second point according to the adjustment parameter. The computation unit further generates a control program that centers an ablation profile on the third point. The control unit controls the corneal ablation laser according to the control program.

8 Claims, 10 Drawing Sheets

(52) U.S. Cl.
CPC ..... *G01B 9/02049* (2013.01); *G01B 9/02091* (2013.01); *A61F 2009/00844* (2013.01); *A61F 2009/00846* (2013.01); *A61F 2009/00851* (2013.01); *A61F 2009/00872* (2013.01); *A61F 2009/00897* (2013.01)

(58) Field of Classification Search
CPC . A61F 2009/00855; A61F 9/008–2009/00897; A61B 3/102
USPC .......................................................... 606/4–6
See application file for complete search history.

(56) References Cited

U.S. PATENT DOCUMENTS

| | | | |
|---|---|---|---|
| 2004/0199149 A1* | 10/2004 | Myers | A61F 9/008 606/4 |
| 2005/0137586 A1 | 6/2005 | Gray et al. | |
| 2009/0033867 A1* | 2/2009 | Dai | A61F 9/00806 351/205 |
| 2010/0114076 A1 | 5/2010 | Reinstein et al. | |
| 2010/0211054 A1* | 8/2010 | Lemonis | A61B 3/112 606/5 |
| 2011/0034911 A1* | 2/2011 | Bischoff | A61F 9/00827 606/4 |

FOREIGN PATENT DOCUMENTS

| | | |
|---|---|---|
| EP | 1985269 A1 | 10/2008 |
| WO | 2009101696 A1 | 8/2009 |

OTHER PUBLICATIONS

Wikipedia; Digital image processing; from Nov. 29, 2011, downloaded on May 31, 2018; 4 pages; Retrieved from website: https://en.wikipedia.org/w/index.php?title=Digital_image_processing&oldid=463167638.

Samuel Arba-Mosquera et al.; "Analysis of the effects of Eye-Tracker performance on the pulse positioning errors during refractive surgery"; Journal of Optometry (www.journalofoptometry.org); available online Feb. 11, 2012; pp. 31-37; Elsevier Doyma.

Wikipedia; Eye tracking; from Mar. 14, 2012, downloaded on Apr. 30, 2018; 7 pages; Retrieved from website: https://en.wikipedia.org/w/index.php?title=Eye_tracking&oldid=481812744.

Dianne Anderson; "Understanding Corneal Topography"; Paraoptometric Resource Center; 12 pages.

* cited by examiner

TECHNIQUE FOR CONTROLLING A CORNEAL ABLATION LASER

CROSS REFERENCE TO RELATED APPLICATIONS

This application is a section 371 national stage phase of International Application No. PCT/EP2012/001727, filed 20 Apr. 2012, titled "TECHNIQUE FOR CONTROLLING A CORNEAL ABLATION LASER," which is hereby incorporated by reference in its entirety.

TECHNICAL FIELD

The present disclosure generally relates to a technique for controlling a laser ablation of the eye. Particularly, the disclosure is directed to a technique for centering the laser ablation profile relative to the eye.

BACKGROUND

Refractive eye surgery relates to a change of refractive properties of the eye, e.g., by remodeling the cornea as one of the optical components of the eye. As an example, LASIK applies ultraviolet laser light for the remodeling. The present disclosure can be applied to the LASIK technique as well as the PRK and EPI-LASIK technique.

The cornea is remodeled according to an ablation profile, which is a 3-dimensional sub-volume of the cornea that is to be removed. A sequence of laser pulses interacts with the stroma of the cornea to ablate living tissue in a precise manner. In controlling the laser light acting on the cornea, a center of ablation is a crucial reference point. The sequence of laser pulses is applied relative to the ablation center. Existing systems for refractive surgery center the ablation profile to the pupil center. This is true for systems, which may perform a treatment of myopia, hyperopia, or astigmatism without import of diagnostic data, e.g., topographic data or wavefront data. However, the pupil center can shift relative to the cornea as the iris of the eye astringe or dilates. Techniques for compensating such a pupil center shift are described in European Patent EP 1 985 269 B1.

Some known systems allow for manually changing the ablation center away from the pupil center. For example, a surgeon can manually aim at centering the ablation profile on a visual axis of the eye. Such a centering offside the pupil center can be essential for patients exhibiting a high deviation between the pupil center and the visual axis, which typically includes cases of hyperopic eyes. However, the manual shifting of the ablation center away from the pupil center is based on a subjective visual estimate of the surgeon as well as the limitation of the instruments, e.g., the microscope resolution, arrangement and alignment. Also, the mere fact that the change is performed manually can imply uncertainty or add to an inaccuracy of the ablation result. Further, the manual shift is time consuming and requires additional effort by the surgeon.

SUMMARY

Accordingly, there is a need for a technique that determines or assists in determining a location of a laser ablation profile of the eye.

According to one aspect, a device for controlling a corneal ablation laser is provided. The device comprises: a parameter interface adapted to receive an adjustment parameter; a first determination unit adapted to determine a first point on a corneal surface; a second determination unit adapted to determine a second point on the corneal surface that is different from the first point; a computation unit adapted to determine a third point on a line between the first point and the second point according to the adjustment parameter and to generate a control program, wherein the control program centers an ablation profile on the third point; and a control unit adapted to control the corneal ablation laser according to the control program.

Throughout, the expression "corneal surface" may encompass an "anterior corneal surface" of an eye. Alternatively or in addition, the expression "corneal surface" may encompass a "corneal surface under a flap". The flap may be created in a LASIK procedure. Expressions of the form "at least one of A and B" encompass "A", "B", "A or B", or "A and B". The interface and the units are collectively referred to as components. Some or all of the components may be implemented in hardware, software or a combination thereof.

The computation unit may further be adapted to determine the line. The third point may be restricted to the line. The third point may be restricted to a position in between the first point and the second point. The line may be on the corneal surface. The corneal surface may be curved. The line may be geodesic on the corneal surface. The geodesic may be defined on the corneal surface by the first point and the second point. The geodesic may be the shortest path on the corneal surface between the first point and the second point.

Alternatively or in addition, the line may be a projection of the geodesic defined on the corneal surface through the first point and the second point. The line may be projected in a plane. The plane may be parallel to the corneal plane. The plane may be perpendicular to an optical axis of the corneal ablation laser or an optical axis of the eye. The plane may be tangential to the corneal surface. The line may be a straight line in the plane.

A pair of coordinates may be defined in the plane. The coordinates may be Cartesian coordinates, e.g., X and Y. Alternatively or in addition, the coordinates may be polar coordinates, e.g., r and phi. An origin of the coordinates (e.g., $X=0$ and $Y=0$, or $r=0$) may correspond to a pupil center. The coordinates may be defined independent of a state of the pupil. The coordinates may be defined relative to the eye, e.g., relative to the cornea. The origin and/or orientation of the coordinates may be defined by reference to the limbus of the eye.

A corneal topography may be represented by a profile of height. The topography of the corneal surface may be represented by a height function, e.g., $H(X,Y)$. Alternatively or in addition, spatial coordinates may be defined. The coordinates may include the Cartesian coordinates, e.g., X, Y and Z. The Z-coordinate (e.g., a vector $\partial/(\partial Z)$) may be perpendicular to the plane. For example, $Z=H(X,Y)$ may represent the corneal surface. The topography of the cornea, or any other structure of the eye including in the cornea, may be represented by a function $\rho(X,Y,Z)$. The function can be a density function or any other measure of signal strength.

The centering may include a coordinate transformation of the ablation profile. The centering may include a shift of the ablation profile on the corneal surface. Alternatively or in addition, the centering may include a rotation of the ablation profile about a center of corneal curvature and/or about the pupil center.

The control unit may be connected or connectable to the corneal ablation laser. The corneal ablation laser may include a laser light source and optical means. The optical means may be adapted to at least one of direct and focus light received from the laser light source towards the corneal surface. The control unit may be connected to the laser light source for generating pulses of light. The laser light source may include an excimer laser. Alternatively or in addition, the control unit may be connected to the optical means.

The adjustment parameter may represent a single degree of freedom. The adjustment parameter may be the only degree of freedom of the third point. The adjustment parameter may represent a single value. The adjustment parameter may represent a percentage value. The adjustment parameter may be equal to 0% for centering the ablation profile on the first point and may be equal to 100% for centering the ablation profile on the second point, or vice versa. Alternatively, a dedicated scale may be used for the adjustment parameter, e.g., the adjustment parameter may be defined in the range from 0 to 1, from 1 to 12, or from 0 to 15. The adjustment parameter may be linearly related to a distance from at least one of the first point and the second point. The adjustment parameter may assume one of a discrete set of values. By way of example, the adjustment parameter may selectively assume one of the values of 0%, 20%, 40%, 60%, 80% and 100% or in-between these values, e.g., 23.5%. The adjustment parameter may be restricted to values representing the third point between the first point and the second point. For example, the values of 0% and 100% may be excluded, i.e., may not be assumed by the adjustment parameter.

The second point may be a corneal apex, corneal vertex, the coaxially sighted corneal reflex (LCR) or a point in between. Alternatively or in addition, the second point may be determined by a visual axis of the eye. The corneal apex may be determined as the point of maximum height in the topography data or may be determined as the minimum thickness of the cornea. Alternatively or in addition, the corneal apex may be determined as the point of maximum surface curvature of the cornea. The corneal vertex may be the point of intersection where a straight line through the center of curvature of the corneal surface perpendicularly intersects the corneal surface. The line of LCR joins the fixation target and the center of curvature of the anterior corneal surface and is thus normal to the cornea and considered the Purkinje reflex on the surface of the cornea. The line may be defined between the corneal apex, the corneal vertex or LCR with the pupil center. The line may include an apex segment and a vertex segment. The apex segment may be a straight line or geodesic between the first point and the corneal apex. The vertex segment may be a straight line or geodesic between the first point and the corneal vertex. Alternatively, the second point can be the mid-point between corneal apex and corneal vertex. It is also possible to use any other point between corneal apex and corneal vertex as the second point.

The device may further comprise at least one of a topography data interface adapted to receive topography data of the corneal surface and a measurement unit adapted to measure the topography data. The topography data may include the corneal topography over the plane or over the corneal surface. The topography data may include height values of the corneal surface as a function of X and Y, e.g., the function H(X,Y). The topography data may be represented by contour lines or a contour map. The topography data may include thickness values from the cornea, e.g., from the stroma. The topography data may include tomography data. The topography data may further indicate a structure and/or quantify dimensions of the anterior chamber of the eye, e.g., by means of the function ρ(X,Y,Z). The topography data interface may be coupled or coupleable to a diagnostic device. The diagnostic device may measure the topography by means of at least one of keratoscopy, slit projection or optical pachymetry, ultrasound pachymetry, a Scheimpflug measurement, and wavefront analysis, optical low coherence reflectometry or optical coherence tomography or a combination thereof. The keratoscopy may include projecting and observing Placido rings on the corneal surface. The person skilled in the art will appreciate that the data can be taken with different suitable devices.

The second determination unit may determine the second point based on the topography data. The second determination unit may be integrated in the measurement unit or in the computation unit. Alternatively, the measurement unit may provide coordinates of the second point and the determination by the second determination unit may include receiving the coordinates.

The first point may be the pupil center. The pupil may be defined as the aperture enclosed by the iris. The pupil center may be the (e.g., projected) geometric center of the boundary defined by the iris. By way of example, the pupil center may be the center of a circle fitted to the boundary defined by the iris. An entrance pupil center as a point within the eye may be projected along a pupillary axis onto the corneal surface, which may define the pupil center.

The device may further comprise an eye tracker adapted to track the first point, wherein the first determination unit is connectable to or included in the eye tracker. The first determination unit may include an eye tracker interface, which may be coupled or coupleable to the eye tracker. The eye tracker may include a camera. The camera may be directed towards the eye or the cornea. The camera may capture one or more of the cornea, the iris and the pupil. The first determination unit may be adapted to track a motion of the eye, e.g., the cornea based on a video signal from the camera. The eye tracker may track the position and/or orientation of the eye. The eye may be tracked in real-time. The camera may provide an image of the eye.

The tracking may be based on structures of the eye, e.g. the iris, pupil, blood vessels or any other structure captured by the camera. The tracking may be initialized by comparing the real-time image to a reference image. The reference image may be taken during measuring of the topography data. Six degrees of freedom may be tracked. The tracking may determine at least one of an X- Y-, or Z-translation, an X- or Y-roll (which is also referred to as a rotation by the X- or Y-axis), and a tilt. The tilt is also referred to as cyclotorsion or a rotation by the Z-axis. The cyclotorsion is a rotation of the eye around its anteroposterior axis. The X-axis may coincide with a transversal axis or nasal-temporal axis. The Y-axis may coincide with a longitudinal axis or superior-inferior axis. The Y-axis is also referred to as vertical axis, independent of whether a patient is standing or lying. The Z-axis may coincide with a sagittal axis, anterior-distal axis or anterior-posterior axis. In terms of the device, the Z-axis may coincide with the optical axis of the corneal ablation laser or the optical axis of the eye.

The computation unit may be further adapted to compute the ablation profile taking into account that the center of the ablation profile is on the line. The computation of the ablation profile may account for a thinnest point or a thinnest portion of the cornea that could be covered by the ablation profile when the center of the ablation profile is on some point on the line. Other points of the cornea, which are outside the ablation profile whenever the center of the ablation profile is on the line, can be ignored in the computation of the ablation profile. The ablation profile may be independent of the adjusting parameter. The ablation profile may be determined prior to at least one of the reception of the adjustment parameter and the generation of the control program. The independence may be achieved by computing the ablation profile in conformance with a thinnest point or a thinnest portion of the cornea covered when considering all potential center positions on the line.

The thinnest point or the thinnest portion of the cornea may be included in or derived from the topography data. The thinnest point or the thinnest portion may be on the order of 300 μm. At least in some embodiments, determining the ablation profile in conformance with the thinnest point or the thinnest portion of the cornea may allow freely selecting the adjustment parameter, e.g., without a restriction due to insufficient cornea thickness at a border area of the cornea.

The computation unit may compute the ablation profile based on the topography data. The ablation profile may indicate or correspond to a reduction in cornea thickness as a function of X and Y. The reduction may correspond to a difference between an ideal or target cornea data and the topography data as measured or received. The ablation profile may be computed according to a refractive correction target. The refractive correction target may aim at fully or partially compensating a refractive error of the eye or of the cornea. The refractive error may include at least one of axial myopia, axial hyperopia and astigmatism. The computation unit may further be adapted to determine the refractive correction target based on the topography data.

The control program may perform a number of ablation steps at various X-Y-positions by means of the control unit. X-Y-positions that are subsequently applied to the cornea by the corneal ablation laser may be spaced apart. Two application of the corneal ablation laser according to the control program may be time-displaced by a minimum relaxation time. The minimum relaxation time may allow for local cooling of the cornea in view of the laser induced optical breakdown. For completion of the control program, the corneal ablation laser may be applied to each X-Y-position listed in the control program for the number of ablation steps defined by the control program.

The parameter interface may include a display adapted to prompt a user for entering the adjustment parameter. The user may select or shift the third point. The selection may be restricted to the line or to a plane spanned by the vertex, the apex and the LCR. Alternatively or in addition, the adjustment parameter may be entered numerically and/or graphically. The prompt may include a bar and an indicator of the parameter slidable on the bar.

The adjustment parameter may be predefined in the absence of a user input, which may also refer to a default value. For example, the parameter interface may predefine a value of the adjustment parameter as an initial value. The predefined value may be 60% of the distance from the first point e.g., the pupil center towards the second point e.g., the corneal apex. Alternatively or in addition, computation unit may further be adapted to estimate the adjustment parameter so that the third point approximates or coincides with a scotopic pupil center, a photopic pupil center, and a mesopic pupil center of the eye.

The computation unit may be further adapted to output, on the display or a dedicated display, a view of the corneal surface superimposed by at least one of the first point, the second point, the third point, the line, and an area indicating the ablation profile. The topography data or any other data provided by the measurement unit, or any other diagnostic device, may be superimposed. In one embodiment, the display is a screen. The dedicated display may be included in the optical path of an operation microscope.

The computation unit may be further adapted to compute an adjustment vector pointing from the first point to the second point. The line may be represented by the adjustment vector. The line may additionally be represented by the first point.

The computation unit may be further adapted to scale the adjustment vector according to the adjustment parameter. The third point may be represented by the scaled adjustment vector. The third point may additionally be represented by the first point. The third point may be represented by a vector sum of coordinates of the first point and the scaled adjustment vector. The ablation profile may be centered on the third point by shifting the ablation profile according to the scaled adjustment vector.

The control program may shift the adjustment vector according a Pupil Center Shift Compensation (PCSC). The computation unit may receive the PCSC from the eye tracker. The PCSC may compensate for a shift of the pupil center, e.g., due to pupillary response. Shifting the adjustment vector may include vectorially adding up the PCSC and the scaled adjustment vector. Alternatively or in addition, the computation unit may further be adapted to shift the ablation profile according the PCSC. In any case, the control program may apply the shift compensation in real-time.

The control program may rotate the adjustment vector according a Cyclotorsion Alignment (CTA). The CTA may correspond to an ocular cyclotorsion and/or may be signaled by the eye tracker to the computation unit. Alternatively or in addition, the computation unit may further be adapted to rotate the ablation profile according the CTA. In any case, the control program may apply the rotation in real-time.

According to another aspect, a method of generating a control program for controlling a corneal ablation laser is provided. The method comprises the steps: receiving an adjustment parameter; determining a first point on a corneal surface; determining a second point on the corneal surface that is different from the first point; computing a third point on a line between the first point and the second point according to the adjustment parameter; and generating a control program that centers an ablation profile on the third point.

The method may further comprise the step of controlling the corneal ablation laser according to the control program.

According to a further aspect, a computer program product is provided. The computer program product comprises program code portions for performing one or more of the steps of one or more of the method aspects described herein when the computer program product is executed on one or more computing devices. The computer program product may be stored on a computer readable recording medium. Alternatively or in addition, the computer program may be provided for download in a computer network, e.g., the Internet.

BRIEF DESCRIPTION OF THE DRAWINGS

In the following, the invention will be described in more detail with reference to exemplary embodiments illustrated in the drawings, wherein FIG. 1 schematically illustrates the structure of an eye in a section parallel to the transverse plane;

FIG. 8 (labeled as FIGS. 8A and 8B) schematically illustrates a variant of the parameter interface shown in FIG. 7.

DETAILED DESCRIPTION

In the following description, for purposes of explanation and not limitation, specific details are set forth, such as specific device configurations and specific reference points on a cornea of an eye in order to provide a thorough understanding of the technique disclosed herein. It will be apparent to one skilled in the art that the technique may be practiced in other embodiments that depart from these specific details. While the following embodiments will primarily be described in relation to a corneal vertex or corneal apex or both, it will be readily apparent that the technique described herein may also be practiced using different reference points and/or different definitions of the reference points.

Those skilled in the art will further appreciate that the methods, steps, functions and components explained herein may be implemented using individual hardware circuitry, using software functioning in conjunction with a programmed microprocessor or general purpose computer.

Figure 1:
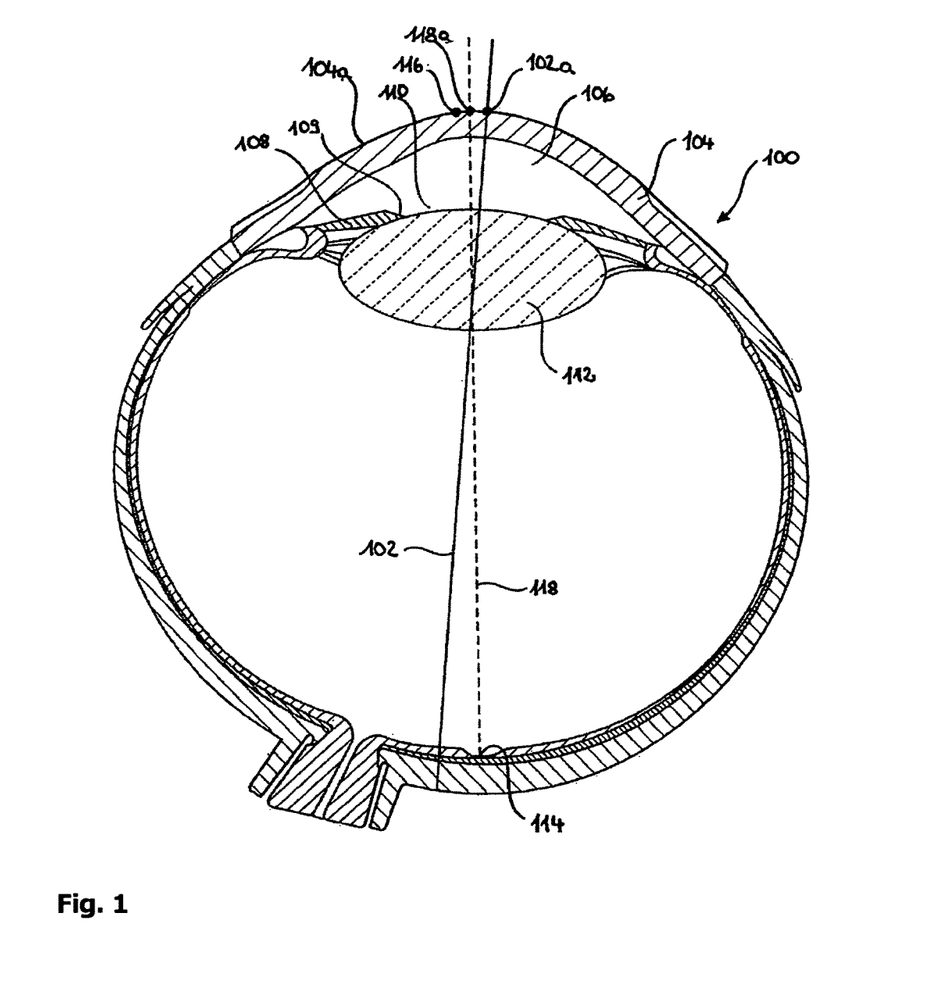

FIG. 1 shows a schematic cross section of a human eye 100 parallel to the transverse plane including an optical axis 102 of the eye 100. The eye 100 shows a cornea 104 with an anterior chamber 106, an iris 108, which edge 109 forms the boundary of a pupil 110, further with a lens 112, a fovea 114, an optical axis 102 and a visual axis 118. The optical axis 102 intersects the front surface 104a of the cornea 104 at the location 102a. The visual axis 118 intersects the front surface of the cornea 104 at the location 118a, which is known as the vertex. An apex 116 can be defined as the highest anterior point of the cornea 104, whereby the apex 116 does not coincide with the intersection 102a of the optical axis 102. In general, the apex 116 of the cornea 104 is located neither at the location 102a nor at the location of the vertex 118a, such that the point of intersection 118a of the visual axis is located between the apex 116 and the point of intersection 102a of the optical axis with the corneal surface 104a.

Figure 2:
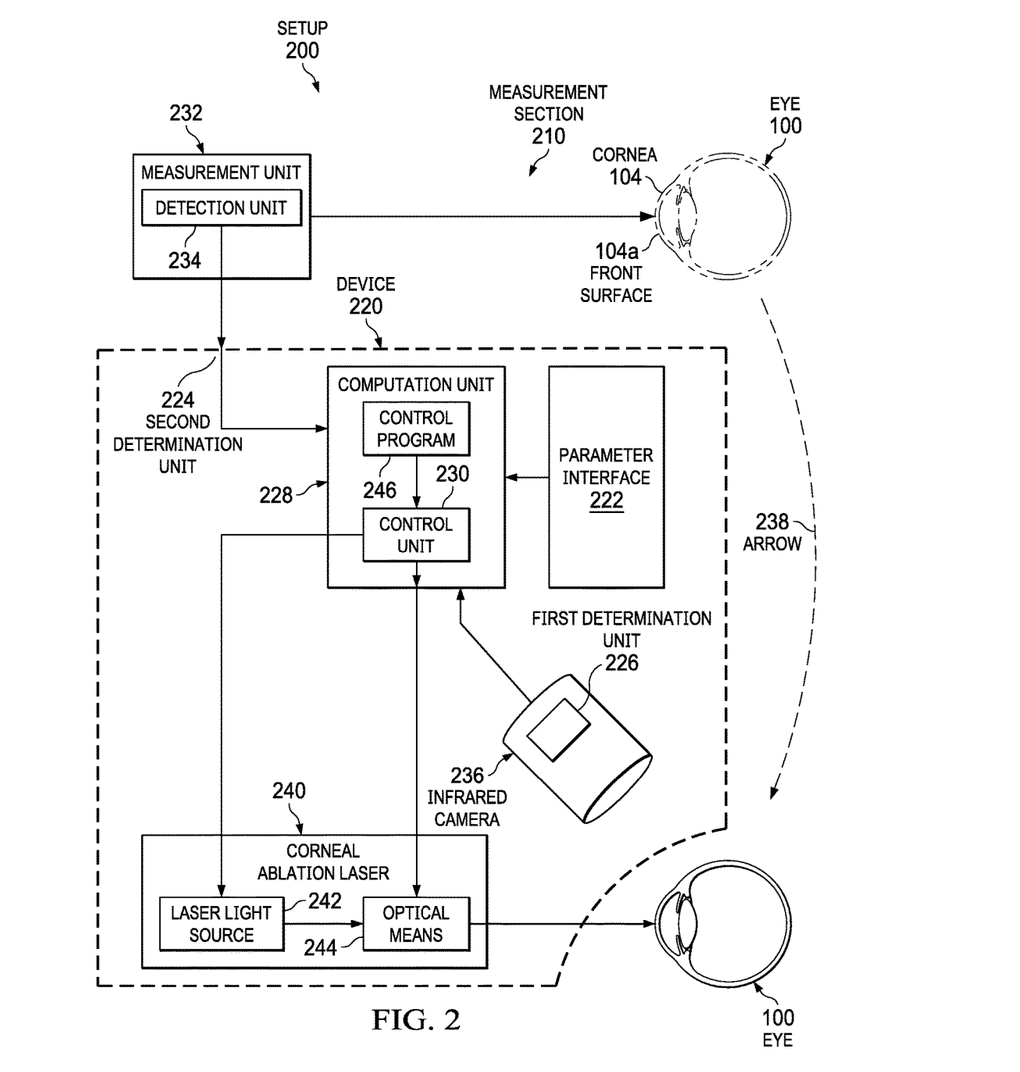
FIG. 2 schematically illustrates a first embodiment of a device for controlling a corneal ablation laser.

FIG. 2 schematically illustrates a setup 200 comprising a measurement section 210 and a device 220 for controlling a corneal ablation laser 240. The device 220 comprises a parameter interface 222, a first determination unit 226, a second determination unit 224, a computation unit 228, and a control unit 230. In this embodiment, the second determination unit 224 includes an interface. The control unit 230 is integrated in the computation unit 228. A measurement unit 232 in the measurement section 210 is connected to the second determination unit 224. The measurement unit 232 measures topography data of the corneal surface 104a of the cornea 104 of the eye 100. The measurement 232 includes a detection unit 234 adapted to detect the apex 116 using the topography data. The detection unit 234 provides coordinates of the detected apex 116 on the corneal surface 104a to the second determination unit 224.

The device 220 further comprises an infrared camera 236. The first determination unit 226 and the infrared camera 236 are collectively referred to an eye tracker. In this embodiment, the first determination unit 226 is integrated in the infrared camera 236. After the measurement, a patient is moved from the measurement section 210 to the device 220 as indicated by an arrow 238. The infrared camera 236 captures the iris 108 and the pupil 110 of the eye 100. A real-time video signal provided by the camera 236 is analyzed by the first determination unit 226. The first determination unit 226 detects the pupil center 102a as a projection of the cornea 104a, based on the video signal. The first determination unit 226 provides coordinates of the pupil center 102a to the computation unit 228.

The computation unit 228 is provided with coordinates of the pupil center 102a as a first point by the first determination unit 226. The computation unit 228 is further provided with coordinates of the apex 116 as a second point by the second determination unit 224. The vertex 118a can also be detected and used as the second point. The coordinates of both the first point and the second point are relative to the cornea 104. This is achieved by using a limbus of the eye 100 as a reference structure that defines the coordinate system. For high accuracy of the coordinates, the limbus is directly used as the reference structure when detecting the first point, and optionally, the second point.

The embodiment of the device 220 shown in FIG. 2 further includes an ablation laser 240. The ablation laser 240 includes a laser light source 242 and optical means 244. The computation unit 228 computes and stores a control program 246. The control unit 230 is connected to the laser light source 242 and the optical means 244. The execution of the control program 246 causes the control unit 230 to trigger the generation of laser pulses by the laser light source 242. The optical means 244 receive and transversely deflect the laser light pulses. The deflection is controlled by the control unit 230 in synchronization with the pulse generation. Upon execution of the control program 246 the ablation laser 240 outputs a sequence of the laser pulses, which interact with the cornea 104 at a plurality of spots according to an ablation profile.

Figure 3:
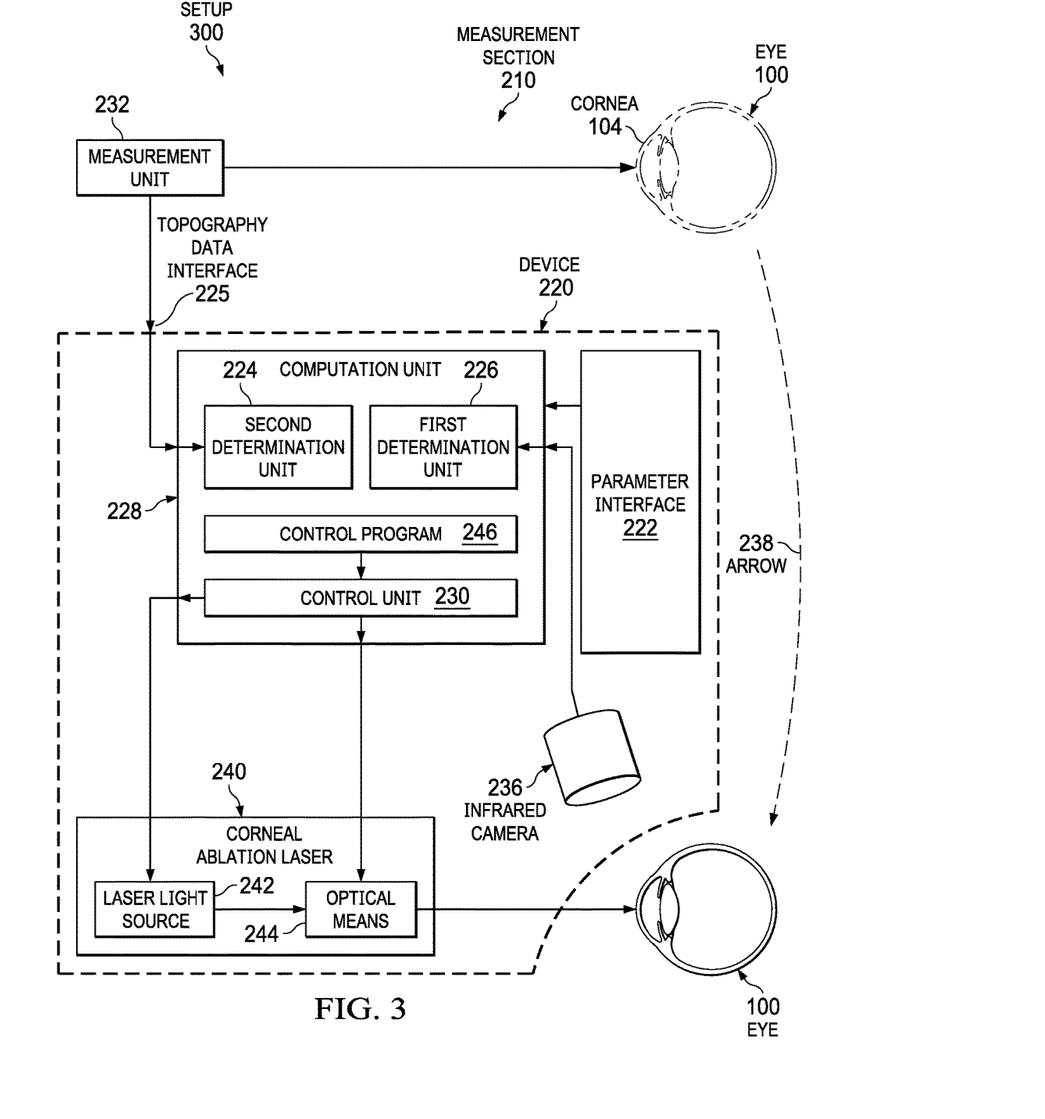
FIG. 3 schematically illustrates a second embodiment of a device for controlling a corneal ablation laser having a higher degree of integration as compared to the device shown in FIG. 2.

FIG. 3 shows another embodiment of a device 220 for controlling a corneal ablation laser. The embodiment of the device 220 shown in FIG. 3 has corresponding and/or interchangeable components as indicated by reference numbers described above with reference to FIG. 2. The embodiment of the device 220 shown in FIG. 3 differs from the one of FIG. 2 in that the functionality of the detection unit 234 shown in FIG. 2 is included in the second determination unit 224. The second determination unit 224 is integrated into the computation unit 228. The measurement unit 232 provides topography data (which is also referred to as diagnostic data) to the second determination unit 224 as raw data via a topography data interface 225 (which is also referred to as a diagnostic data interface). The detection functionality uses computational resources of the computation unit 228 to detect the corneal apex 116 and/or the corneal vertex 118a based on the topography data.

The first determination unit 226 is also integrated into the computation unit 228, which receives the video signal in real-time from the infrared camera 236. For a compact embodiment, the first determination unit 226 and the second determination unit 224 are implemented by means of routines encoded in memory of the computation unit 228.

Figure 4:
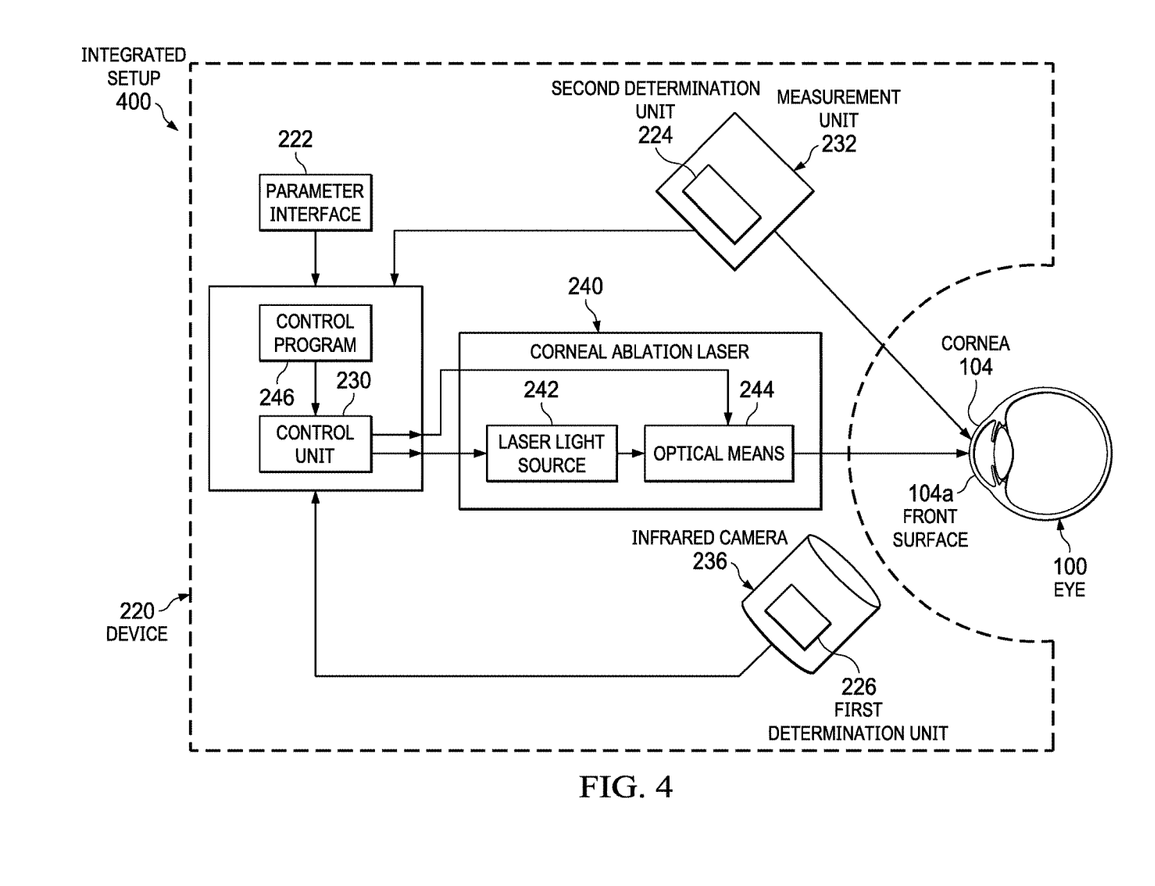
FIG. 4 schematically illustrates a third embodiment of a device for controlling a corneal ablation laser having a still higher degree of integration as compared to the device shown in FIG. 3.

FIG. 4 schematically illustrates a third embodiment of a device 220 for controlling a corneal ablation laser 240 in an integrated setup 400 for both measurement and laser ablation. Corresponding or interchangeable components described with reference to the setup 200 or 300 are indicated by corresponding reference signs in the integrated setup 400. The device 220 shown in FIG. 4 differs from the device 220 shown in FIG. 2 in that the measurement unit 232 is integrated into the device 220. The patient does not have to be moved from a measurement section 210 for a subsequent laser ablation based on the measurement. Optionally, as shown in FIG. 4, the second determination unit 224 providing the detection functionality for the second point is integrated in the measurement unit 232.

Figure 5:
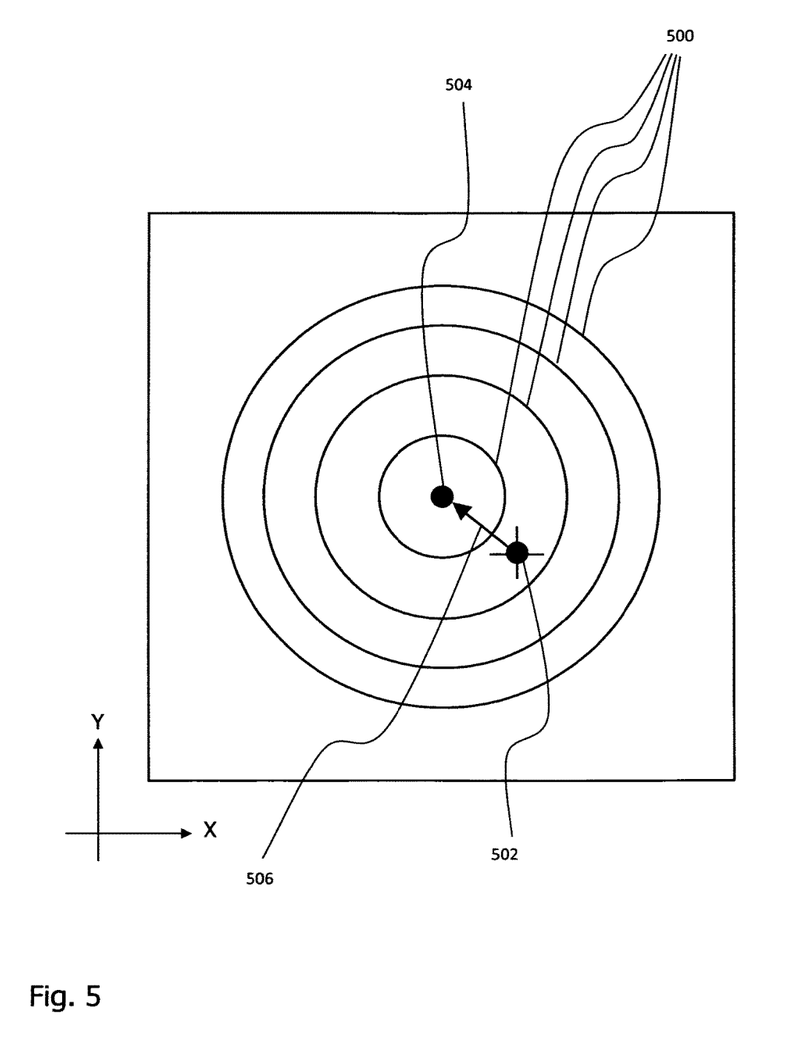
FIG. 5 schematically illustrates coordinates of a first point and a second point that can be used by any one of the devices shown in the FIG. 2, 3 or 4.
Figure 6:
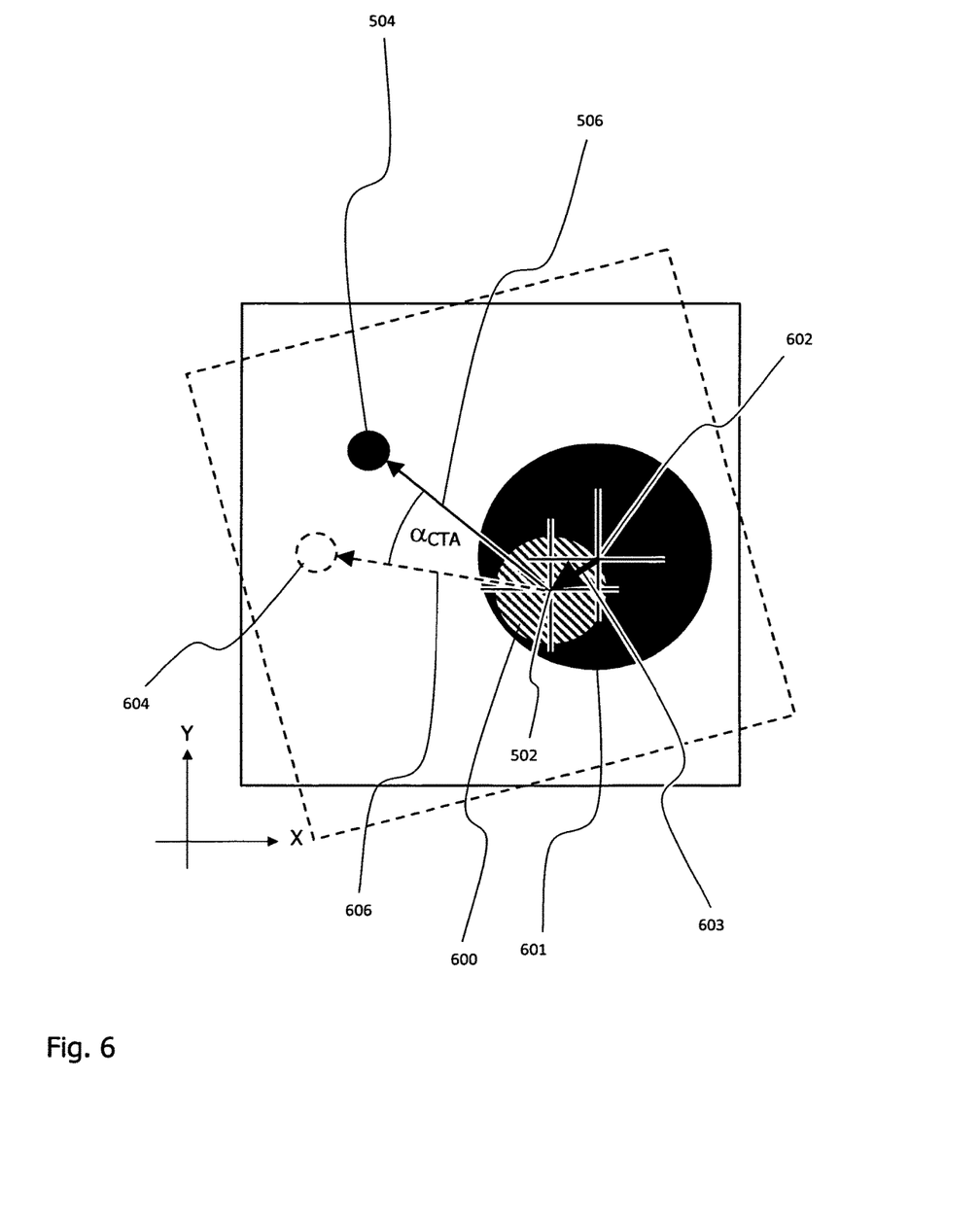
FIG. 6 schematically illustrates a shift and a rotation applied to the coordinates shown in FIG. 5.

The generation of the control program 246 is described in more detail with reference to the FIGS. 5 and 6. FIG. 5 schematically illustrates the topography data 500 provided by the measurement unit 232. In the example of FIG. 5, the topography data 500 is represented by contour lines. The contour lines result from a profile function Z(X, Y), which indicates the "height" of the corneal surface 104a by means of a coordinate Z. The Z-coordinate may coincide with the optical axis 102. The corneal profile Z(X, Y) is a function of coordinates X and Y in a coronal plane. More precisely, the plane of the coordinates X and Y may be defined relative to the eye 100. For example, the plane may be perpendicular to the optical axis 102. In a reduced embodiment, the plane can be stationary. For example, the plane can be defined relative to the device 220.

The coordinates X and Y within the plane are always defined relative to the eye 100, independent of whether the plane or the Z-axis is defined relative to the eye 100. For example, the first point 502 provided by the first determination unit 226 may define the origin of the coordinates X and Y. The first determination unit 226 of the eye tracker not only defines the origin of the coordinate system but also its orientation. At least one set, e.g., three sets, of raw data provided by the measurement unit 232 are averaged. Based on the averaged data, the topography data 500 is derived. The second point 504 is detected based on the topography data 500. In the example shown in FIG. 5, the second point 504 is the apex 116.

An adjustment vector 506 (also referred to as correlation vector) is computed by the computation unit 228. The adjustment vector 506 points from the first point 502 to the second point 504. In response to the second point provided by the second determination unit 224, the coordinates of the first point 502 are received from the eye tracker and the adjustment vector 506 is computed as a vector difference. Data reception and computation may be repeated, e.g., three times. If the resulting candidate vectors are consistent, the candidate vectors are averaged yielding the adjustment vector 506. The consistency is determined by a variance of the candidate vectors.

The control program continuously repeats the computation of the adjustment vector as the eye tracker detects a movement of the eye. The eye tracker provides the position of the pupil center 102a as the first point 502 based on the detection of six independent degrees of freedom, which is also referred to as a "6D-detection". The 6D-detection accounts for both a movement of the eye 100 and a movement of a head of the patient.

The control program 246 continuously updates the spots of the laser ablation based on the continuously computed adjustment vector 506. FIG. 6 shows in more detail the detection of the first point 502 and the updating of the adjustment vector 506. As is described in European patent EP 1 985 269 B1, a changing size of the pupil 110 may be associated with a shift of the apparent pupil center 102a relative to the cornea 104, which is subject to the laser ablation. The change is indicated by a photopic pupil 600 and a mesopic pupil 601 schematically shown in FIG. 6. The detection unit 234 or the detection functionality included in the second determination unit 224 corrects a deviation between the apparent pupil center 602 and the first point 502 by means of a Pupil Center Shift Compensation (PCSC) 603.

Further, one of the six degrees of freedom detected by the eye tracker indicates a change in the angular orientation of the eye, which is also referred to as cyclotorsion alignment (CTA). The control program 246 corrects the CTA by rotating the coordinate system about the first point 502. By virtue of the rotation by a CTA-angle $\alpha_{CTA}$, a previous second point 604 and a previous adjustment vector 606 are updated in real-time in response to the detected CTA, yielding the second point 504 and the adjustment vector 506.

Figure 7:
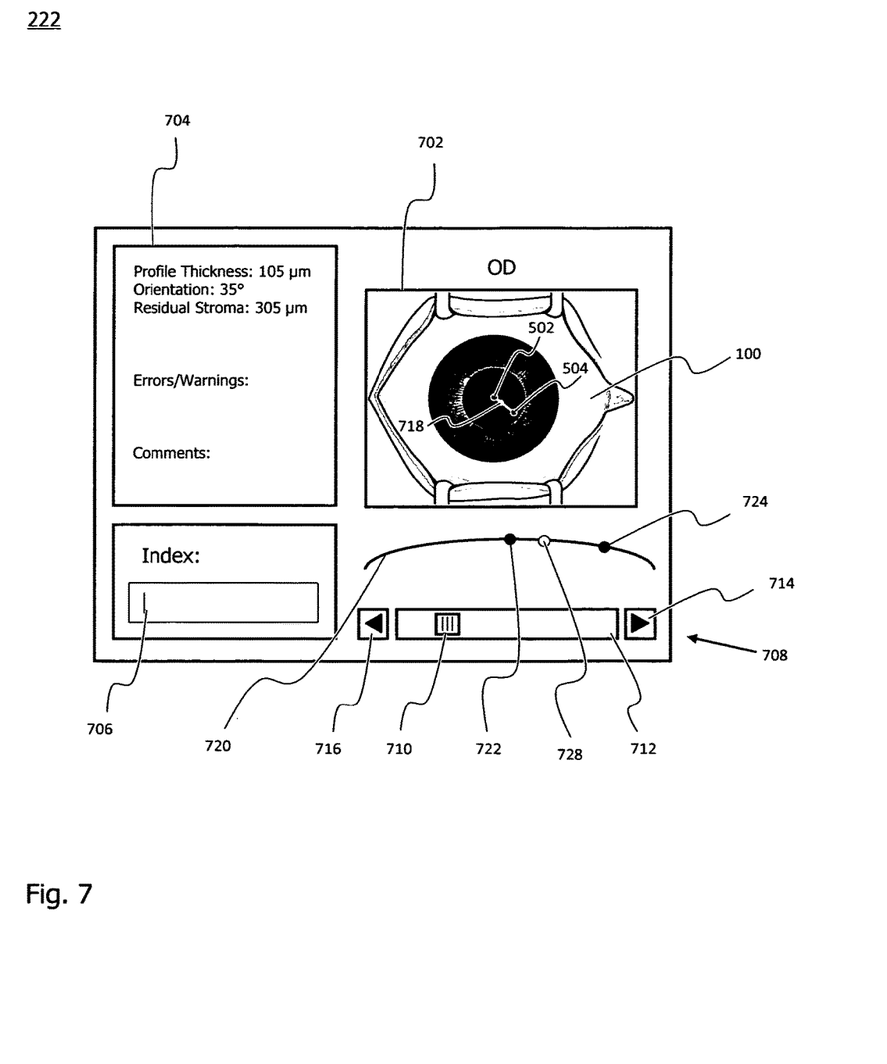
FIG. 7 schematically illustrates a parameter interface that can be included in any one of the devices shown in FIG. 2, 3 or 4.

FIG. 7 schematically illustrates the parameter interface 222 used in each of the setups 200, 300 and 400 of the device 220. The parameter interface 222 allows a user, e.g., a surgeon, to define or alter an adjustment parameter. The parameter interface 222 includes a real-time image 702 of the eye 100, an information window 704, a manual parameter prompt 706 and a scroll bar 708. The scroll bar 708 includes a slider 710 that is shiftable along a bar 712 in response to user input.

The adjustment parameter can be input as index values in the manual user prompt 706. Alternatively, the position of the slider 710 within the bar 712 defines the value of the adjustment parameter. The adjustment parameter can also be changed step by step using an incrementing button 714 or decrementing button 716.

A straight line connecting the first point 502 and the second point 504 is superimposed in the real-time image 702. The computation unit 228 scales the adjustment vector 506 according to the adjustment parameter. A third point 718 is defined on the line by starting at the first point 502 and adding the scaled adjustment vector 506. In other words, the scaled adjustment vector points from the first point 502 to the third point 718. If a maximum value, e.g., 12, is entered at the manual user prompt 706 or the slider 710 is shifted to the right end of the bar 712, the scaled adjustment vector equals the adjustment vector such that the third point 718 coincides with the second point 504. If, on the other hand, a minimum value, e.g., 0, is entered in the manual prompt 706 or the slider 710 is shifted to the left end of the bar 712, the scaling factor for the scaling of the adjustment vector 506 is zero, such that the third point 718 coincides with the first point 502.

For any parameter value between the minimum value and the maximum value, the third point is located on the line in between the first point 502 and the second point 504. The position of the third point 718 on the line between the first point 502 and the second 504 is linearly related to the adjustment parameter. Denoting the first point 502 by P1 and the second point 504 by P2, the third point 718 is $$P3 = P1 + s \cdot \overrightarrow{P1P2},$$

wherein $\overrightarrow{P1P2}$ is the adjustment vector 506 and $s \cdot \overrightarrow{P1P2}$ is the scaled adjustment vector. Denoting the adjustment parameter by p, the minimum value of the adjustment parameter by $p_{min}$ and the maximum value by $p_{max}$, the scaling factor s is computed according to $$s = (p - p_{min})/(p_{max} - p_{min}).$$

It is noted that the scaling factor s is the adjustment parameter, if $p_{max}=1$ and $p_{min}=0$. The third point is on the line and spaced apart from the first point 502 by a distance $$|s*\overrightarrow{P1P2}|=s*|\overrightarrow{P1P2}|=[(p-p_{min})*|\overrightarrow{P1P2}|]/(p_{max}-p_{min}),$$

wherein $|\overrightarrow{P1P2}|$ is the length of the line, i.e. the distance between the first point 502 and the second point 504. In other words, the third point is on the line and spaced apart from the second point 504 by a distance $$[(p_{max}-p)*|\overrightarrow{P1P2}|]/(p_{max}-p_{min}),$$

In an advanced variant, the adjustment parameter p is non-linearly related to the position of the third point 718 on the line. A non-linear and strictly monotonically increasing control function $$s=f(p)$$

depending on the adjustment parameter p can assist in more accurately positioning the third point 718 in an important area of the corneal ablation, for example in the vicinity of the visual axis 124. Denoting the adjustment parameter corresponding to the third point 718 closest to the visual axis 124 or on the visual axis 124 by $p_{VA}$, the non-linear function f(p) may increase slower in the vicinity of $p_{VA}$ than outside the vicinity of $p_{VA}$. By way of example, the non-linear function $$s=[(p-p_{VA})^3-(p_{min}-p_{VA})^3]/[(p_{max}-p_{VA})^3-(p_{min}-p_{VA})^3]$$

allows fine-tuning the third point 718 near the visual axis 124.

The adjustment parameter is initialized, so that the third point 718 is shifted on the line, e.g., 60% off the first point 502 towards the second point 504, i.e., so that s=0.6. The initial value of the adjustment parameter is applied for the generation of the control program 246 in the absence of a user input.

The parameter interface 222 shown in FIG. 7 further includes a schematic cross section of the cornea 104, wherein a curved line 720 illustrates the corneal surface 104a in the cross section. Points 722, 724 and 728 represent the first point 502, the second point 504 and the third point 718, respectively.

Whenever an adjustment parameter is entered at the manual prompt 706, the slider 710, the third point 718 superimposed in the real-time image 702 and the schematic representation including the point 728 are updated. Similarly, the numerical value shown at the manual prompt 706, the superimposed third point 718 and the point 728 of the schematic representation are also updated in response to a user input at the scroll bar 708.

During the execution of the control program 246, the apparent adjustment vector 606 is rotated according to the CTA-angle $\alpha_{CTA}$ and scaled according to the adjustment parameter. The sum of the PCSC vector 603 and the rotated and scaled adjustment vector 506 is continuously computed, so that the third point 718 is updated in real-time based on the apparent pupil center 602 and the vector sum of the PCSC vector 603 and the rotated and scaled adjustment vector, or based on the pupil center after compensation as the first point 502 and the rotated and scaled adjustment vector 506. The control program 246 controls by means of the control unit 230 the ablation laser 240, so that the laser ablation follows a real-time motion of the eye detected by the eye tracker and is continuously centered on the third point 718 on the line between the first point 502 and the second point 504 in accordance with the adjustment parameter. The third point 718 is thus set by means of the parameter interface 222 prior to the laser ablation and the control program maintains the third point 718 as the center of the ablation profile relative to the cornea 104 throughout the laser ablation.

Figure 8A:
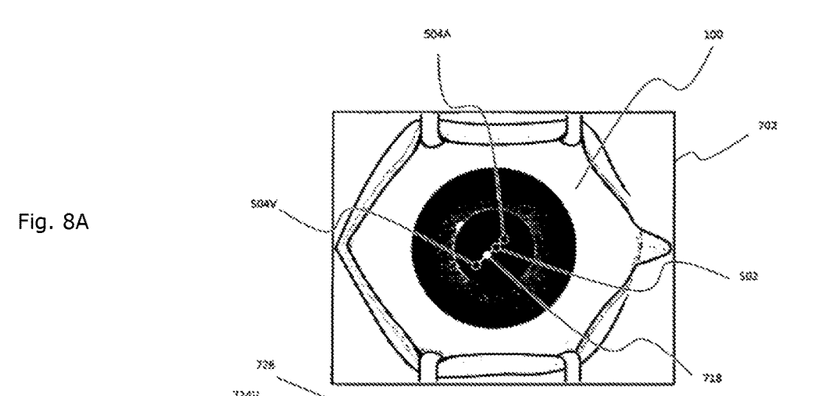
Figure 8B:
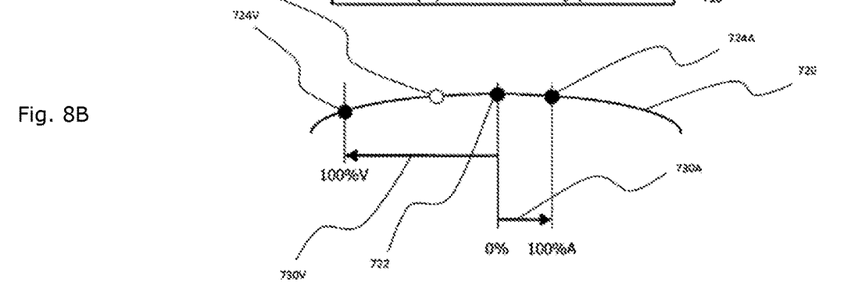

FIG. 8 shows a variant of the parameter interface 222, which exhibits the case of a keratoconus. Further details of the real-time image 702 and the schematic representation of the cross section along the line 720 are schematically illustrated in FIG. 8. The details can in part or completely replace corresponding features of the parameter interface 222 shown in FIG. 7. Other features of the parameter interface 222 have been omitted in FIG. 8 for the clarity of the illustration. The real-time image 702 of the eye 100 includes a superposition of the first point 502 and two second points 504A and 504V. The first point 502 is defined by the PCSC-corrected pupil center 136. The second point 504A is the apex 116 and the second point 504V is defined by the vertex 118a. The line thus includes two segments: an apex segment from the first point 502 to the second point 504A and a vertex segment from the first point 502 to the second point 504V. Typically, the apex segment and the vertex segment of the line are essentially parallel, such that the line including both segments is essentially straight. It is, however, not required that the line includes only parallel segments. For example, the line may have a kink at the first point 502. In the exemplary situation schematically illustrated in FIG. 8, the third point 718 is on the vertex segment.

The schematic representation of the cross section along the line and perpendicular to the corneal surface 104a is shown in the lower half of FIG. 8. The schematic cross section includes the curved line 720 indicating the corneal surface 104a in the cross section, the point 722 representing the first point 502, the points 724A and 724V representing the second points 504A and 504V, respectively, and the point 728 indicating the position of the third point 718.

The adjustment parameter can be entered at the manual prompt 706 by means of percentage values. An additional letter A or V attached to the percentage sign indicates the apex segment or vertex segment, respectively. Accordingly, a percentage value suffixed by "% A" indicates a shift from the first point 502 towards the second point 504A as indicated by an arrow 730A. Similarly, a percentage value concluded by "% V" defines an adjustment parameter for the third point 718 shifted in a direction 730V from the first point 502 towards to the second point 504V.

The computation unit 728 computes corresponding adjustment vectors 506 for the directions 730A and 730V and scales the adjustment vector 506 indicated by the letter "A" or "V" according to the percentage value. The third point 718 on the line is thus computed by starting with coordinates of the first point 502 and adding in the length and direction of the indicated scaled adjustment vector 506.

Figure 9:
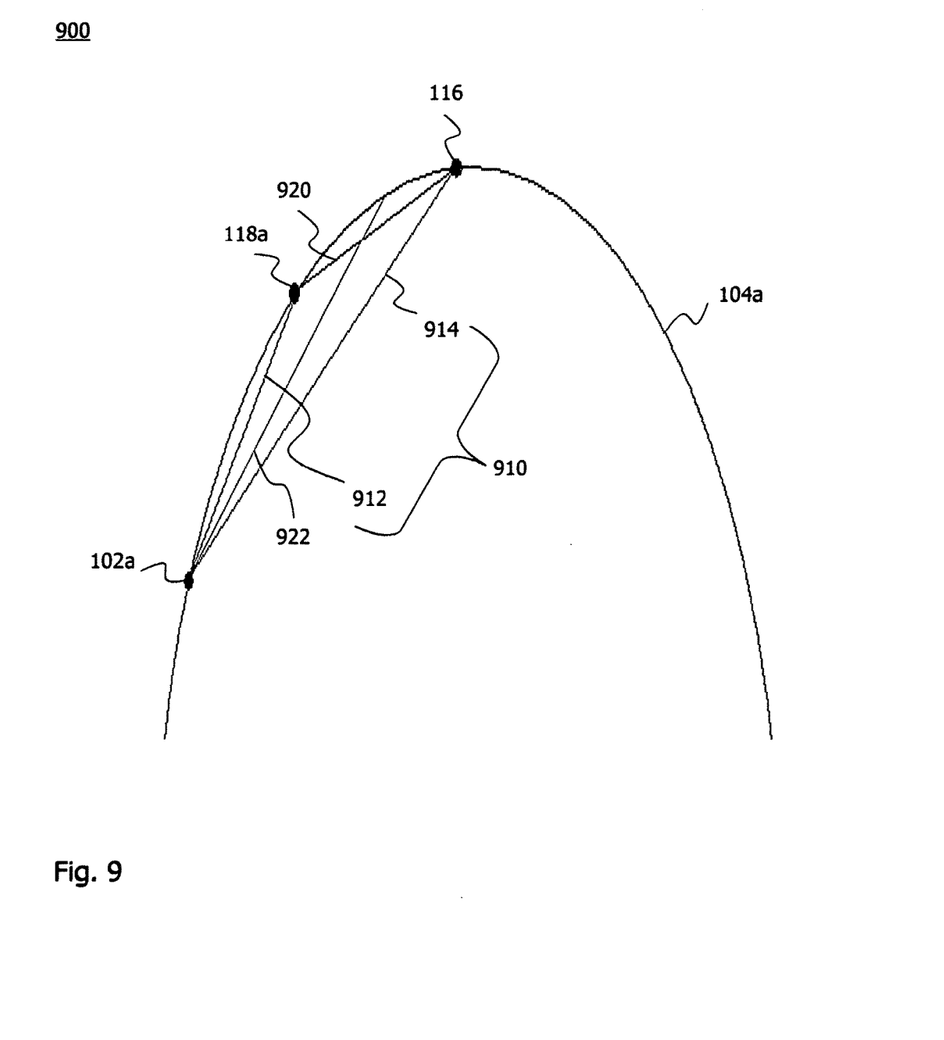
FIGS. 9 and 10 schematically illustrate exemplary definitions of the second point.

FIG. 9 schematically illustrates an exaggerated cross-sectional view 900 perpendicular to the corneal surface 104a. The cross-sectional view 900 shows an exemplary relative arrangement of the pupil center 102a, the corneal vertex 118a and the corneal apex 116. The line 910 (which may include two or more segments 912, 914) shows the line of alignment of the ablation profile (which may also be referred to as an applanation profile). The second point may be any point between the apex 116 and the vertex 118a, and optionally after projection to the corneal surface 104a or to the plane, e.g., the plane defined by the coordinate system. By way of example, the mid-point may function as the second point. For instance, the mid-point may be defined by the intersection of the first auxiliary line 920 and the second auxiliary line 922. The first auxiliary line 920 may be the straight line connecting the apex 116 and the vertex 118a. The second auxiliary line 922 may be the angle bisector between the segments 912 and 914. Optionally, the point of intersection may be projected to the corneal surface 104a or to the plane.

Figure 10:
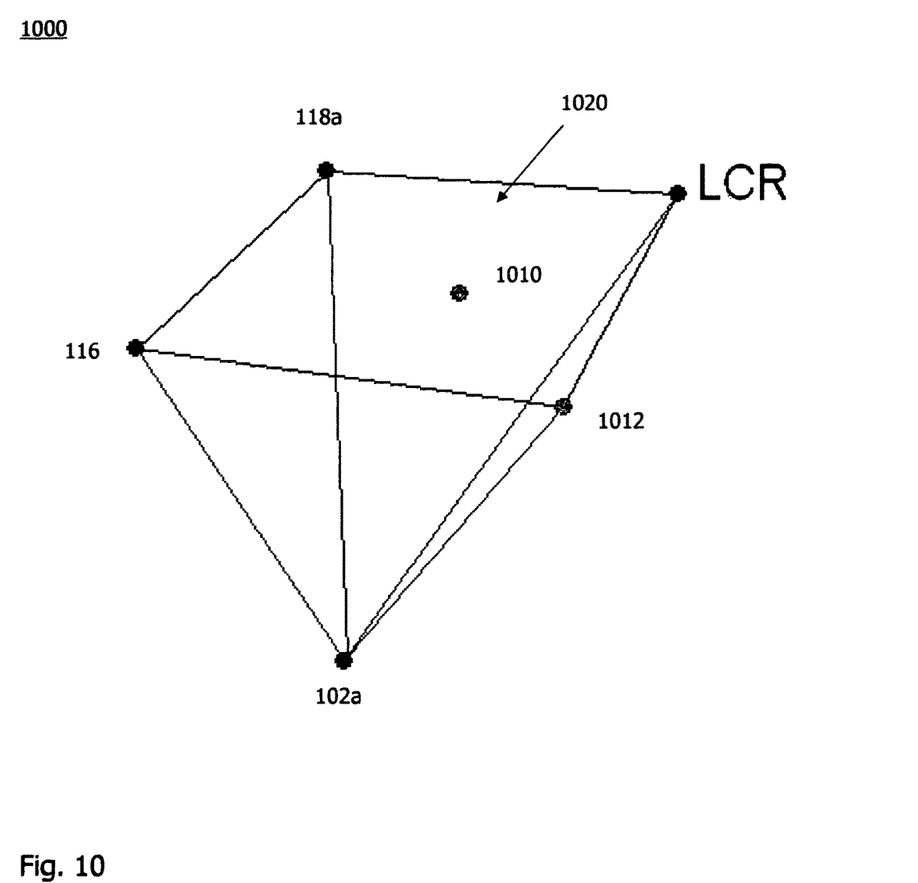

FIG. 10 schematically illustrates further locations 1010 and 1012 that can be used for the second point. As a difference to the definition of the second point described above with reference to FIG. 9, the relation shown in FIG. 10 is three dimensional. Accordingly, each point is defined by corresponding three-dimensional coordinates in space. The three points corresponding to the apex 116, the vertex 118a and the LCR define a plane 1020. Each point in the plane 1020 spanned by the apex 116, the vertex 118a and LCR may be used for the second point.

As has become apparent from above description of exemplary embodiments and variants thereof, the technique allows shifting the center of a corneal laser ablation in a guided manner on a line, which is fixed relative to the cornea, even if the cornea is moving due to ocular movement while the cornea is subject to the laser ablation. The automatic determination of the first point and the second point eliminates a subjective estimate of the optimal center position for the laser ablation. Furthermore, the center position can be quantified or even be predefined by means of the adjustment parameter. While the line has been described as including one or two segments, the technique is not limited to a certain number of segments or a certain number of second points used for defining the segments of the line. The line may also be star-shaped. For example, the line may comprise three or more segments, each segment having the first point as a first endpoint and a different one of the second points as a second endpoint.

In the foregoing, principles, embodiments and various modes of implementing the technique disclosed herein have exemplarily been described. However, the present invention should not be construed as being limited to the particular principles, embodiments and modes discussed above. Rather, it will be apparent that variations and modifications may be made by a person skilled in the art without departing from the scope of the present invention as defined in the following claims.

The invention claimed is:

1. A device for controlling a corneal ablation laser, the device comprising:
   the corneal ablation laser;
   a display adapted to receive an adjustment parameter;
   an eye tracker comprising a camera and a first determination unit adapted to:
      track a motion of an eye; and
      determine a first point on a corneal surface of the eye, the first point comprising a pupil center;
   a corneal topography diagnostic device comprising a measurement unit and a second determination unit adapted to:
      measure corneal topography over the corneal surface; and
      determine a second point on the corneal surface that is different from the first point, the second point comprising a corneal apex or a corneal vertex of the corneal surface;
   a computer adapted to:
      compute an adjustment vector pointing from the first point comprising the pupil center to the second point comprising the corneal apex or the corneal vertex;
      scale the adjustment vector according to the adjustment parameter to determine a third point on a line between the first point and the second point according to the adjustment parameter; and
      generate a control program that centers an ablation profile on the third point; and
   the computer comprising a laser controller adapted to control the corneal ablation laser according to the control program.

2. The device of claim 1, wherein the adjustment parameter represents a single degree of freedom.

3. The device of claim 1, wherein the diagnostic device determines the second point based on diagnostic data.

4. The device of claim 1, wherein the computer is further adapted to compute the ablation profile taking into account that the centering of the ablation profile is on the line.

5. The device of claim 1, wherein the display is adapted to prompt a user to enter the adjustment parameter.

6. The device of claim 5, wherein the computer is further adapted to output, on the display or a dedicated display, a view of the corneal surface superimposed by at least one of the first point, the second point, the third point, the line, and an area indicating the ablation profile.

7. The device of claim 1, wherein the control program shifts the adjustment vector according to a pupil center shift compensation.

8. The device of claim 1, wherein the control program rotates the adjustment vector according to a cyclotorsion alignment.

* * * * *